(12) United States Patent
Zhan et al.

(10) Patent No.: US 8,586,788 B2
(45) Date of Patent: Nov. 19, 2013

(54) METHOD FOR PRODUCING OF ULTRA-CLEAN AND HIGH-PURITY ELECTRONIC GRADE ACETIC ACID

(75) Inventors: Jiarong Zhan, Baoshan Shanghai (CN); Curtis Dove, Baoshan Shanghai (CN); I-Hsing Lin, Baoshan Shanghai (CN)

(73) Assignee: Asia Union Electronic Chemical Corporation Shanghai, Baoshan Shanghai (CN)

( * ) Notice: Subject to any disclaimer, the term of this patent is extended or adjusted under 35 U.S.C. 154(b) by 310 days.

(21) Appl. No.: 12/914,690

(22) Filed: Oct. 28, 2010

(65) Prior Publication Data

US 2012/0067714 A1 Mar. 22, 2012

(30) Foreign Application Priority Data

Sep. 17, 2010 (CN) .......................... 2010 1 0284450

(51) Int. Cl.
*B01D 3/00* (2006.01)
*B01D 69/12* (2006.01)
*B01D 71/06* (2006.01)
*C07C 51/42* (2006.01)
*C07C 53/08* (2006.01)

(52) U.S. Cl.
USPC ............ 562/607; 159/DIG. 27; 159/DIG. 28; 203/1; 203/16; 203/39; 203/DIG. 16; 210/295; 210/641; 210/651; 210/653; 210/500.27; 562/608

(58) Field of Classification Search
USPC ......... 159/47.1, DIG. 27, DIG. 28; 203/1, 16, 203/39, 100, DIG. 16; 210/295, 640, 641, 210/651, 653, 500.27; 562/607, 608
See application file for complete search history.

(56) References Cited

U.S. PATENT DOCUMENTS

| | | | | |
|---|---|---|---|---|
| 3,750,735 A | * | 8/1973 | Chiang et al. | 159/49 |
| 4,170,551 A | * | 10/1979 | Honour | 122/446 |
| 4,788,043 A | * | 11/1988 | Kagiyama et al. | 422/292 |
| 4,879,041 A | * | 11/1989 | Kurokawa et al. | 210/640 |
| 4,953,694 A | * | 9/1990 | Hayashi et al. | 202/180 |
| 5,585,527 A | * | 12/1996 | Marker | 203/18 |
| 5,868,906 A | * | 2/1999 | Adams et al. | 203/18 |
| 6,733,637 B1 | * | 5/2004 | Burton et al. | 203/14 |
| 8,075,740 B2 | * | 12/2011 | Bailie et al. | 202/176 |
| 2009/0275786 A1 | * | 11/2009 | Shirasawa et al. | 568/699 |

* cited by examiner

*Primary Examiner* — Virginia Manoharan
(74) *Attorney, Agent, or Firm* — Nath, Goldberg & Meyer; Joshua B. Goldberg; Megan B. Doughty

(57) ABSTRACT

A method for producing of ultra-clean and high-purity electronic acetic acid is disclosed. The method including following steps: Step 1, industrial acetic acid is fast distilled; Step 2, filtering the fraction by membrane of 0.05~0.3 μm aperture; Step 3, rectification; Step 4, membrane filtration again. Due to the adoption of the technical scheme above, the ultra-clean and high-purity electronic grade acetic acid which purity is 99.8% is produced. The content of single metal ion is lower than 1 ppb and the content of particulates which is ≥0.5 μm is lower than 5 pcs/ml. The method of the invention will help to reduce energy consumption, to simplify the operation, and to achieve the high security.

8 Claims, 1 Drawing Sheet

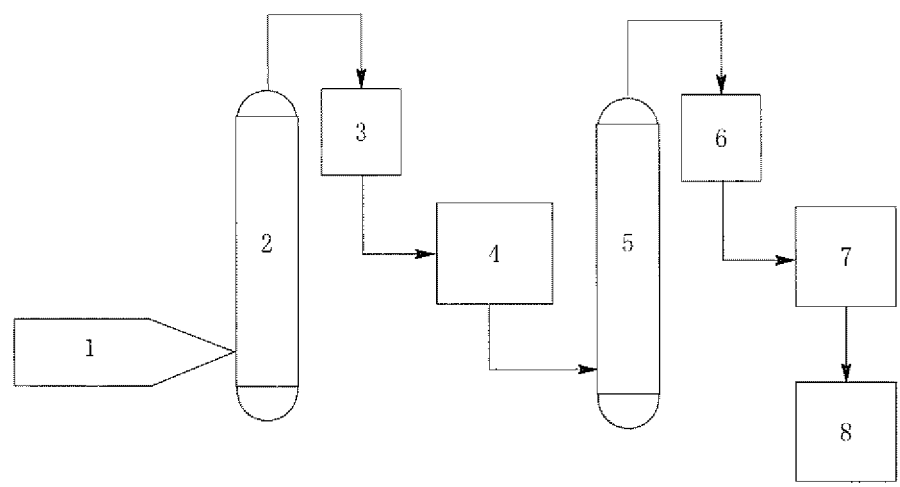

METHOD FOR PRODUCING OF ULTRA-CLEAN AND HIGH-PURITY ELECTRONIC GRADE ACETIC ACID

FIELD OF THE INVENTION

The present invention relates to a method for producing electronic grade chemicals. In particular, the present invention is directed to a method for producing Ultra-clean and High-purity electronic grade acetic acid.

BACKGROUND OF THE INVENTION

Electronic grade acetic acid is an important solvent and indispensable electronic chemical in the electronic industry. Some particulates, metal ions, unreacted raw materials, and intermediate products or by-products will be in the acetic acid because of the raw materials and equipments used during production, transportation and storage. The existence of these impurities, in particular metal ions, can lead to Oxidation Induced Stacking Faults (OISF) so that the PN Junction Leakage Current increases, Breakdown occurs, and the life of current carrier shortens. Even a small quantity of metal ions or particulates can destroy the whole circuit when the line width of the integrated circuit is thin. Therefore the purity of electronic chemicals is critical to ensure the development of a super large-scale integrated circuit. Therefore, the purity of electronic chemicals must meet the demands of nanometer-grade IC.

The key to the production of liquid Ultra-clean and High-purity Reagents (or Process Chemicals) such as acetic acid is ensuring the content of impurities (such as metal ions etc.) and granularity is in conformity with the standard of requirement. Presently, the main producing methods include ionized sub-boiling distillation, azeotropic distillation, (multistage) rectification, and chemical treatment, etc. However, there isn't a satisfactory method for producing electronic grade acetic acid.

Multistage rectification, such as the two-stage rectification method and equipment disclosed in Chinese patent No.CN1285560C, to produce acetic acid in conformity with the SEMI-C7 standard is the most commonly used method for producing of ultra-clean and high purity acetic acid. The multistage rectification results in continuous production over a long period of time, but requires heavy energy consumption and high risk.

Chinese patent No.CN100372586C disclosed a method and equipment for producing ultra-clean and high-purity acid. The method and equipment is composed of a barbed rectification tower and a filled tower in series to produce electronic acid such as hydrochloric acid and acetic acid. This method improves the conventional method. However, the internal structure of the required equipment is complicated.

SUMMARY OF THE INVENTION

The present invention provides a method for producing ultra-clean and high-purity electronic grade acetic acid. The metal ions and particulates can be removed effectively because of the combination of distillation, membrane filtration, and rectification. The ultra-clean and high-purity electronic grade acetic acid is produced via a simple operation comprising low energy consumption and high safety.

The method of the invention for producing ultra-clean and high-purity acetic acid includes following steps:

Step 1, fast distilling industrial acetic acid and collecting a fraction at a rate of ≥20 L/min to remove the unreacted raw materials, intermediate products or by-products; the optimized rate of fraction collection is 20-50 L/min.

Step 2, filtering the fraction collected in step 1 through a membrane having 0.05-0.3 μm apertures;

Step 3, rectifying the colature and collecting the fraction;

Step 4, filtering the fraction collected in step 3 through a membrane having 0.05-0.3 μm apertures, and collecting the colature to produce ultra-clean and high-purity electronic grade acetic acid.

In Step 1, the optimized distillation temperature is 130-140° C.

In Step 2, the optimized membrane used is a β-cyclodextrin composite membrane.

In Step 3, the optimized rectification is atmospheric rectification under 125-135° C., and the fraction is collected when the steam is at a temperature in a range of 117.5-118.5° C.

In Step 4, the optimized membrane used is an 18-crown-6 ether composite membrane.

The optimized filter velocity of the fraction through the β-cyclodextrin or the 18-crown-6 composite membrane is 1-5 L/h.

In the preferred embodiment, the rectification column in the present invention is a packed tower.

The optimized packing is the mixture of High Density Polyethylene (HDPE) and Polyfluoroalkoxy (PFA).

The optimized weight ratio between HDPE and PFA is 10-15:1.

The method of the present invention removes most of organic impurities such as formic acid and acetaldehyde through the fast distillation before rectification. In addition, the cost of distillation is much lower than rectification.

Because most of the impurities are removed, the purity of the acetic acid before rectification is increased. So the working difficulty of rectification is greatly decreased. In addition, the energy consumption and risk of the method are lower than that of the conventional method.

The membrane filter used to remove metal ions is much simpler in operation, costs less, and is more environmentally friendly than rectification. In addition, the filter does not only remove metal ions, but also remove particulates.

The PFA used as packing in the packed tower has the advantage of good separating efficiency. Furthermore, the addition of HDPE greatly decreases the cost but doesn't decrease the separation result.

Overall, the method for producing ultra-clean and high-purity acetic acid has the advantage of simple operation, low energy consumption and low cost. The purity of the product is 99.8%, the content of single metal ion is lower than 1 ppb, and the content of particulates which are ≥0.5 μm is 2 pcs/ml.

BRIEF DESCRIPTION OF THE DRAWINGS

FIG. 1 illustrates the process of the method of the present invention.

DETAILED DESCRIPTION OF THE INVENTION

A better understanding of the present invention is obtained when the following non-limiting detailed description is considered in conjunction with FIG. 1. In FIG. 1, reference number 1 is the industrial acetic acid; reference number 2 is a distillation column; reference number 3 is a cooling column; reference number 4 is a β-cyclodextrin composite membrane filter; reference number 5 is a rectifying column; reference number 6 is a cooling column; reference number 7 is an 18-crown-6 composite membrane filter; and reference number 8 is a reservoir.

Embodiment 1:

Step 1, Industrial acetic acid is fast distilled to remove the unreacted raw materials and intermediate products or by-products generated during synthesis of acetic acid.

Most of the impurities can be removed through distillation, which has a lower cost simpler operation than rectification.

The temperature of distillation can be selected within the range of 130-140° C., and the rate of fraction collection is in the range of 20-50 L/min to quicken distillation, save time, and increase productivity.

Step 2, filtering the fraction collected in step 1 through a membrane having 0.05-0.3 μm apertures. In order to avoid breakage or a worse filtering result due to high pressure, the filtration velocity must be kept in a range of 1-5 L/h.

Step 3, rectifying the colature at 125-135° C. and atmospheric pressure, and collecting a fraction when the steam temperature is in a range of 117.5-118.5° C.

The packed tower with the packing working as gas-liquid contactor can be used as the rectification column because of its advantage of high yield, separation efficiency, low energy consumption, and small pressure loss, etc.

The packing that supplies the gas-liquid contact surface to mass and heat transfer is the core of the packed tower. PFA (Polyfluoroalkoxy), which is the polymer of corrosion resistance and high temperature resistance, leads to good separating efficiency as packing.

The mixture of HDPE (High Density Polyethylene) and PFA can be used as packing also. And the optimized weight ratio between HDPE and PFA is 10-15:1. The cost of the packing reduces to 1/50-1/100 because of the low-cost of the HDPE. Also, the addition of HDPE does not decrease the separating efficiency of PFA.

Step 4, filtering the fraction collected in Step 3 through the membrane having 0.05-0.3 μm apertures and collecting the colature to get the ultra-clean and high-purity electronic grade acetic acid.

Similar to that of Step 2, the filtration velocity of the fraction filtration in step 4 is in a range of 1-5 L/h.

In order to produce ultra-clean and high-purity acetic acid, metal ions are removed by rectification and particulates are removed by the membrane filter.

Embodiment 2:

Step 1, fast distilling industrial acetic acid to remove the unreacted raw materials and intermediate products or by-products generated during synthesis of acetic acid; and collecting the fraction.

Step 2, filtering the fraction collected in Step 1 through the β-cyclodextrin composite membrane. The filtration velocity is kept in a range of 1-5 L/h.

β-cyclodextrin is a cyclic oligosaccharide, and it is tubbish or tubular. The β-cyclodextrin composite membrane can remove the heavy metal ions because of the particularly molecule structure.

Hence, the particulates, and some metal ions simultaneously, are removed by the β-cyclodextrin composite membrane. Therefore, the difficulty of the next rectification is reduced.

The production of the β-cyclodextrin composite membrane comprises: Solid Kaolin clay, main constituents of which are $SiO_2$, $Al_2O_3$ and $H_2O$, is grinded with β-cyclodextrin to 200-300 mesh fines, and mixed homogeneously with binder (polyvinyl alcohol for example) to get base (semifinished product). The base is dried at a low temperature and sintered at 200-250° C. to get a composite membrane of the β-cyclodextrin and Kaolin clay carrier having 0.05-0.3 μm apertures.

Step 3, rectifying the colature at 125-135° C. and atmospheric pressure, and collecting the fraction when the steam temperature is in a range of 117.5-118.5° C.

Step 4, filtering the fraction collected in step 3 through a membrane having 0.05-0.3 μm apertures and keeping the filtration velocity in a range of 1-5 L/h.

Embodiment 3:

Step 1, fast distilling industrial acetic acid to remove the unreacted raw materials and intermediate products or by-products generated during synthesis of acetic acid; and collecting the fraction.

Step 2, filtering the fraction collected in Step 2 through the membrane having 0.05-0.3 μm apertures and keeping the filtration velocity in a range of 1-5 L/h.

Step 3, rectifying the colature at a temperature of 125-135° C. and atmospheric pressure, and collecting fraction when the steam temperature is in a range of 117.5-118.5° C.

Step 4, filtering the fraction collected in Step 3 through an 18-crown-6 ether composite membrane, and keeping the filtration velocity in a range of 1-5 L/h.

The 18-crown-6 ether, which is also called 1,4,7,10,13,16-hexaoxacyclooctadecane, is a crown ether. The diameter of the 18-crown-6 ether cyclic molecule is equivalent to the diameter of a potassium ion. Therefore the 18-crown-6 ether can be complex with light metal ions, such as potassium ions and sodium ions, and remove these ions. Hence the particulates and some residual metal ions after rectification are removed simultaneously.

The 18-crown-6 ether composite membrane can be produced by the method for the β-cyclodextrin composite membrane.

At last, the colature is collected to get the ultra-clean and high-purity acetic acid.

Embodiment 4:

Step 1, fast distilling industrial acetic acid to remove the unreacted raw materials and intermediate products or by-products generated during synthesis of acetic acid; and collecting the fraction at a rate of 20-50 L/min.

Step 2, filtering the fraction using a β-cyclodextrin composite membrane, and keeping the filtration velocity in a range of 1-5 L/h.

Step 3, rectifying the colature at a temperature of 125-135° C. and atmospheric pressure, and collecting the fraction when the steam temperature is in a range of 117.5-118.5° C.

Step 4, filtering the fraction through an 18-crown-6 ether composite membrane, and keeping the filtration velocity in a range of 1-5 L/h.

Collecting the colature to get the ultra-clean and high-purity electronic grade acetic acid.

The purity of the acetic acid produced in Embodiment 4 was detected with the following equipment: autotitrator for the content of acetic acid; ICP-MS for the content of cations; turbidimeter and Ultraviolet Spectrophotometer for the content of anions; and Laser Particle Counter for the content of particulates. The testing result of the purity is listed in table 1.

TABLE 1

| purity of the acetic acid produced in Embodiment 4 | | |
| --- | --- | --- |
| Parameter | U.M. | Result |
| Assay($CH_3COOH$) | % | 99.8 |
| Color | APHA | 5 |
| Chloride(Cl) | ppb | 121 |
| Sulfate($SO_4$) | ppb | 234 |
| Phosphate($PO_4$) | ppb | 95 |
| Residue After Evaporation | ppb | 231 |

TABLE 1-continued purity of the acetic acid produced in Embodiment 4

| Parameter | U.M. | Result |
|---|---|---|
| Acetic Anhydride | % | ≤0.1 |
| Aluminum(Al) | ppb | 0.3 |
| Arsenic(As) | ppb | 0.6 |
| Antimony(Sb) | ppb | 0.4 |
| Barium(Ba) | ppb | 0.3 |
| Beryllium(Be) | ppb | 0.7 |
| Bismuth(Bi) | ppb | 0.2 |
| Boron(B) | ppb | 0.1 |
| Cadmium(Cd) | ppb | 0.3 |
| Calcium(Ca) | ppb | 0.6 |
| Chromium(Cr) | ppb | 0.3 |
| Cobalt(Co) | ppb | 0.2 |
| Copper(Cu) | ppb | 0.2 |
| Gallium(Ga) | ppb | 0.4 |
| Germanium(Ge) | ppb | 0.5 |
| Gold(Au) | ppb | 0.1 |
| Indium(In) | ppb | 0.2 |
| Ion(Fe) | ppb | 0.4 |
| Lead(Pb) | ppb | 0.6 |
| Lithium(Li) | ppb | 0.1 |
| Magnesium(Mg) | ppb | 0.3 |
| Manganese(Mn) | ppb | 0.5 |
| Molybdenum(Mo) | ppb | 0.4 |
| Nickel(Ni) | ppb | 0.3 |
| Niobium(Nb) | ppb | 0.6 |
| Potassium(K) | ppb | 0.3 |
| Platinum(Pt) | ppb | 0.2 |
| Silicon(Si) | ppb | 0.3 |
| Silver(Ag) | ppb | 0.4 |
| Sodium(Na) | ppb | 0.7 |
| Strontium(Sr) | ppb | 0.4 |
| Tin(Sn) | ppb | 0.4 |
| Tantalum(Ta) | ppb | 0.4 |
| Titanium(Ti) | ppb | 0.4 |
| Thallium(Tl) | ppb | 0.4 |
| Zinc(Zn) | ppb | 0.5 |
| Zirconium(Zr) | ppb | 0.3 |
| ≥0.3 μm particulates | pcs/ml | 123 |
| ≥0.5 μm particulates | pcs/ml | 2 |
| ≥1.0 μm particulates | pcs/ml | none |

According to the result in table 1, it can be seen that the purity of acetic acid produced is 99.8%, the content of single metal ions is lower than 1 ppb, and the content of particulates which are ≥0.5 μm is 2 pcs/ml. Therefore the product is in conformity with the standard of ultra-clean and high-purity electronic grade acetic acid.

The above description illustrates the subject matter of the application including reagents, equipment, and operation. Any omitted details shall be deemed normal and routine in this field of technology.

It will be understood that the description of the embodiments above is only the illustrations of application, and it does not limit the invention to the specific embodiments illustrated. Numerous other ways of carrying out the method provided by the present invention may be devised by those skilled in the art without departing from the scope of the invention, and they are thus encompassed by the present invention. Thus it should be understood that any identical shifting can be done without departing from the scope of the present invention.

The invention claimed is:

1. A method for producing ultra-clean and high-purity electronic grade acetic acid comprising the following steps:
   step 1: distilling industrial acetic acid, and collecting a fraction at a volumetric rate of ≥20 L/min;
   step 2: filtering the fraction collected in step 1 through a β-cyclodextrin composite membrane having 0.05-0.3 μm apertures and collecting a filtrate;
   step 3: rectifying the filtrate and collecting a fraction;
   step 4: filtering the fraction collected in step 3 through an 18-crown-6 ether composite membrane having 0.05-0.3 μm apertures, and collecting a filtrate to obtain ultra-clean and high-purity electronic grade acetic acid.

2. The method according to claim 1, wherein the fraction is collected at a volumetric rate of 20-50 L/min in step 1.

3. The method according to claim 2, wherein the industrial acetic acid is distilled at a temperature of 130-140° C.

4. The method according to claim 1, wherein a filter velocity of the fraction through the β-cyclodextrin composite membrane and the 18-crown-6 ether composite membrane is 1-5 L/h.

5. The method according to claim 1, wherein the filtrate is rectified at a temperature of 125-135° C. and normal atmosphere, and the fraction is collected when steam is at a temperature in a range of 117.5-118.5° C. in step 3.

6. The method according to claim 5, wherein the filtrate is rectified in a packed tower rectifying column in step 3.

7. The method according to claim 6, wherein the packed tower rectifying column is packed with a mixture of High Density Polyethylene (HDPE) and Polyfluoroalkoxy (PFA).

8. The method according to claim 7, wherein the mixture of HDPE and PFA has a weight ratio of 10-15:1.

* * * * *